(12) United States Patent
Mikolajczyk et al.

(10) Patent No.: US 7,211,397 B2
(45) Date of Patent: May 1, 2007

(54) METHOD OF ANALYZING NON-COMPLEXED FORMS OF PROSTATE SPECIFIC ANTIGEN IN A SAMPLE TO IMPROVE PROSTATE CANCER DETECTION

(75) Inventors: Stephen D. Mikolajczyk, San Diego, CA (US); Harry G. Rittenhouse, Del Mar, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 696 days.

(21) Appl. No.: 10/246,582

(22) Filed: Sep. 18, 2002

(65) Prior Publication Data

US 2003/0059864 A1   Mar. 27, 2003

Related U.S. Application Data

(63) Continuation-in-part of application No. 10/154,715, filed on May 24, 2002, and a continuation-in-part of application No. 09/303,208, filed on Apr. 30, 1999, now Pat. No. 6,482,599, and a continuation-in-part of application No. 09/303,339, filed on Apr. 30, 1999, now Pat. No. 6,423,503.

(51) Int. Cl.
  *G01N 33/53* (2006.01)
(52) U.S. Cl. .......................... 435/7.1; 435/4
(58) Field of Classification Search ............. 424/130.1; 530/387.1, 300; 436/64, 813; 514/2
See application file for complete search history.

(56) References Cited

U.S. PATENT DOCUMENTS

2002/0045198 A1* 4/2002 Mikolajczyk et al. ...... 435/7.23
2004/0214246 A1* 10/2004 Hoesel et al. ............... 435/7.23

OTHER PUBLICATIONS

Mikolajczyk et al. Cancer Res. 2001, 61: 6958-6963.*
Catalona et al. JAMA, 1998, 279 (19): 1542-1547.*
Mikolajczyk, Clinical Biochemistry, 2004, 27: 519-528.*

* cited by examiner

*Primary Examiner*—Larry R. Helms
*Assistant Examiner*—Hong Sang
(74) *Attorney, Agent, or Firm*—Hogan & Hartson LLP

(57) ABSTRACT

Assays for detecting and determining the presence of prostate cancer is provided. The assays are capable of detecting prostate cancer in the population of men with a significantly higher ratio of free PSA to total PSA. The assays are also capable of detecting prostate cancer in the population of men with a low amount of total PSA, i.e., in the range of 2 to 4 ng/ml. In accordance with one embodiment of the present invention, the assay includes the steps of (a) determining the amount of total PSA contained in a biological sample from the patient, (b) determining the amount of free PSA in the sample; and calculating the ratio of the free PSA to the total PSA, (c) determining the amount of pPSA in the sample, (d) determining the amount of BPSA in the sample, (e) determining the amount of inPSA in the sample, and (f) correlating the amount of inPSA contained in the sample to the presence of prostate cancer in the patient by comparing the amount of inPSA to a predetermined value established with control samples of known cancer and benign disease diagnosis, based on both the level of total PSA and the % free PSA.

33 Claims, 16 Drawing Sheets

METHOD OF ANALYZING NON-COMPLEXED FORMS OF PROSTATE SPECIFIC ANTIGEN IN A SAMPLE TO IMPROVE PROSTATE CANCER DETECTION

RELATED INVENTION

This is a continuation-in-part of U.S. application Ser. No. 10/154,715, filed on May 24, 2002, U.S. application Ser. No. 09/303,208, filed on Apr. 30, 1999 now U.S. Pat. No. 6,482,599 and U.S. application Ser. No. 09/303,339, filed on Apr. 30, 1999 now U.S. Pat. No. 6,423,503, the content of which is incorporated herein in its entirety by references.

BACKGROUND OF THE INVENTION

1. Area of the Art

The present invention relates generally to the detection and identification of proteins, as well as various forms and subunits of proteins, which have the potential utility as diagnostic markers. In particular, the present invention relates to the detection or determination of inactive forms of prostate specific antigens in the biological fluid of humans, and methods for the improved detection of prostate cancer.

2. Description of the Related Art

The measurement of serum prostate specific antigen (PSA) is widely used for the screening and early detection of prostate cancer [1–3]. Serum PSA that is measurable by current clinical immunoassays exists primarily as either the free "non-complexed" form (free PSA), or as a complex with $\square_{-1}$antichymotrypsin (ACT) [1–5]. The ratio of free to total PSA in serum has been demonstrated to significantly improve the discrimination of PCa from BPH, with higher ratios correlating with a lower risk of prostate cancer [1–7].

The biological mechanism for the variable levels of free PSA in serum is unknown. The serum PSA that has become complexed is likely to be relatively homogeneous since this represents enzymatically active, intact PSA. The PSA released from the PSA-ACT complex in prostate cancer (PCa) and benign prostate hyperplasia (BPH) serum was found to be indistinguishable from seminal plasma PSA, which confirms this assumption [8]. It follows that free PSA may offer better biochemical insight, and that a characterization of the molecular forms of free PSA could help elucidate their prostatic origin and mechanism of release into the serum.

Various mixtures of PSA containing inactive forms of PSA have been isolated from prostate tissues and seminal plasma. The PSA from BPH tissue has been characterized in a more general way as being more highly internally clipped [9], though no single form or forms of PSA were isolated from the mixture of clipped and unclipped PSA forms studied in this work. PSA in seminal plasma has been separated by chromatographic methods into fractions shown to contain various mixtures of clipped and non-clipped PSA [10]. However, in none of these studies have antibodies been developed to any single form of inactive PSA or have these PSA forms been demonstrated in serum.

In serum, the free (uncomplexed) PSA is now known to be comprised of at least two specific forms of inactive PSA. One form has been identified as the proenzyme, or precursor form of PSA (pPSA), which includes truncated forms of PPSA that are more associated with cancer [11–13]. A second specific form of PSA, called BPSA, is an internally cleaved or degraded form of PSA that is more highly associated with BPH [14;15]. BPSA was isolated and extensively characterized as a homogeneous species of PSA. A detailed review of BPSA and pPSA has been recently published [16].

Another method of describing and measuring sub-populations of free forms of PSA in serum has also been reported by Nurmikko [17]. In this case, intact PSA (PSA-I) is defined as free PSA that is not clipped at Lys145. This assay recognizes free PSA forms that are not internally clipped at Lysine145, the site of the most common form of degraded PSA in seminal plasma. The nature of the PSA measured by this method is not well-defined except that it is not clipped at Lys145. As such, this assay would measure mixtures of pPSA forms in combination with other uncharacterized inactive forms of PSA not clipped at Lys145.

Because the clinically useful concentrations of PSA are present in the serum at less than 10 ng/ml, it is necessary to develop immunoassays or other very sensitive methods to measure the PSA. The current commercial free PSA immunoassays measure the combined sum of all forms of free PSA, levels typically below 2 ng/ml. Antibodies and immunoassays for pPSA, BPSA and PSA-I remain the only reported research immunoassays for measuring sub-forms of free PSA in serum. Therefore, a need exists to develop novel methods for measuring different forms of free PSA, and further study their associations with different prostate disease status.

SUMMARY OF THE INVENTION

One aspect of the present invention provides a method to aid in distinguishing prostate cancer from benign disease in a subject. The method includes the steps of:

a) determining the amount of total PSA contained in a biological sample from the subject;

b) determining the amount of free PSA in the sample; and calculating the ratio of the free PSA to the total PSA;

c) determining the amount of inPSA in the sample; and d) correlating the amount of inPSA contained in the sample to the presence of prostate cancer in the subject by comparing the amount of inPSA to a predetermined value established with control samples of known cancer and benign disease diagnosis, based on both the level of total PSA and the ratio of the free PSA to the total PSA.

Preferably, immunoassays are used for determining different forms of PSA. In accordance with one embodiment of the present invention, the amount of inPSA may be determined by using blocking antibodies specific for pPSA and BPSA to block pPSA and BPSA contained in a sample, and then measuring the amount of free PSA contained in the sample as a way of determining the amount of inPSA. Alternatively, in a different embodiment, the method further comprises the steps of determining the amount of BPSA and pPSA. The amount of inPSA may be determined by subtracting the amount of BPSA and pPSA from the amount of free PSA.

In accordance with embodiments of the present invention, the correlating step may be a step of correlating the amount of inPSA alone or a mathematical combination of inPSA with total PSA, free PSA, BPSA, and pPSA to a predetermining value. The mathematical combination may be addition, subtraction, division, or the combination thereof.

According to the embodiments of the present invention, the total PSA may be at any level below 20 ng/ml, or more preferably below 10 ng/ml, or most preferably in the range of 2.5 to 10 ng/ml. The ratio of free PSA to total PSA may be any range of free PSA that is typically found in patient sera, from 1 to 50%, though in one embodiment of the invention, the preferred range is greater than 20%, and most preferably, greater than 25%. The pPSA may be [−2]pPSA, [−4]pPSA, [−5,−7]pPSA, or the combined sum of these three forms of native and truncated pPSA, indicated as pPSA. The sample may be any physiological fluid, though serum or plasma is preferred.

DETAILED DESCRIPTION OF THE INVENTION

Definitions:

As discussed above, serum prostate specific antigen (PSA) exists in different forms. For the purpose of the present invention, the term "total PSA" refers to all detectable forms of PSA including free PSA and PSA complexed with ACT. The term "free PSA" as used herein refers to PSA that is not complexed to any other protein but is found as the ~30 kDa protein in solution.

One form of free PSA is pPSA or proPSA. pPSA and proPSA as used herein refers to a precursor form of PSA. A full-length precursor form of PSA includes a propeptide of 7 amino acids, APLILSR, which precedes the mature PSA protein of 237 amino acids. The full-length amino acid sequence of a proPSA is known in the art and is fully described in the reference [18], the relevant content of which is incorporated herein by reference. For the purpose of the present invention, the last amino acid "R" of the propeptide sequence is counted as [−1] amino acid. For example, [−7] proPSA is a proPSA with its terminus starting at −7aa of the propeptide. It contains the full-length proPSA. [−5] proPSA indicates that the terminus of the proPSA starts at −5aa of the propeptide, and it contains the last five amino acid sequences of the propeptide sequence of proPSA, etc. For the purpose of the present invention, proPSA of the present invention includes both full-length and truncated forms of proPSA with its terminus started at any amino acid of the propeptide of the proPSA. Examples of proPSA of the present invention include, but are not limited to, [−1]pPSA, [−2]pPSA, [−4] pPSA, [−5]pPSA and [−7]pPSA. For the purpose of the present invention, the term "pPSA" without any prefix always means the sum of [−2]pPSA, [−4]pPSA and [−5,−7]pPSA. [−5, −7]pPSA as used herein refers to the sum of [−5] and [−7] since in some instances antibodies that recognize the [−5] form also recognize the [−7] form.

The proPSA is inactive, i.e., it lacks chymotrypsin-like enzymatic activity and therefore is present in serum as free PSA, not as PSA antichymotrypsin complex. ProPSA of the present invention may be made by methods commonly known in the art, such as, but not limited to, protein purification techniques, recombinant protein techniques, and protein synthesis techniques. The details for producing and detecting proPSA of the present invention are discussed in a co-pending U.S. Patent Application entitled "Forms of Prostate Specific Antigen and Methods for Their Detection," Ser. No. 08/846,408, filed on Apr. 30, 1997, and the co-pending U.S. patent application entitled "METHOD OF ANALYZING PROENZYME FORMS OF PROSTATE SPECIFIC ANTIGEN IN SERUM TO IMPROVE PROSTATE CANCER DETECTION," Ser. No. 08/846,408, filed on May 24, 2002, the relevant contents of which are incorporated herein in its entirety.

Figure 16:
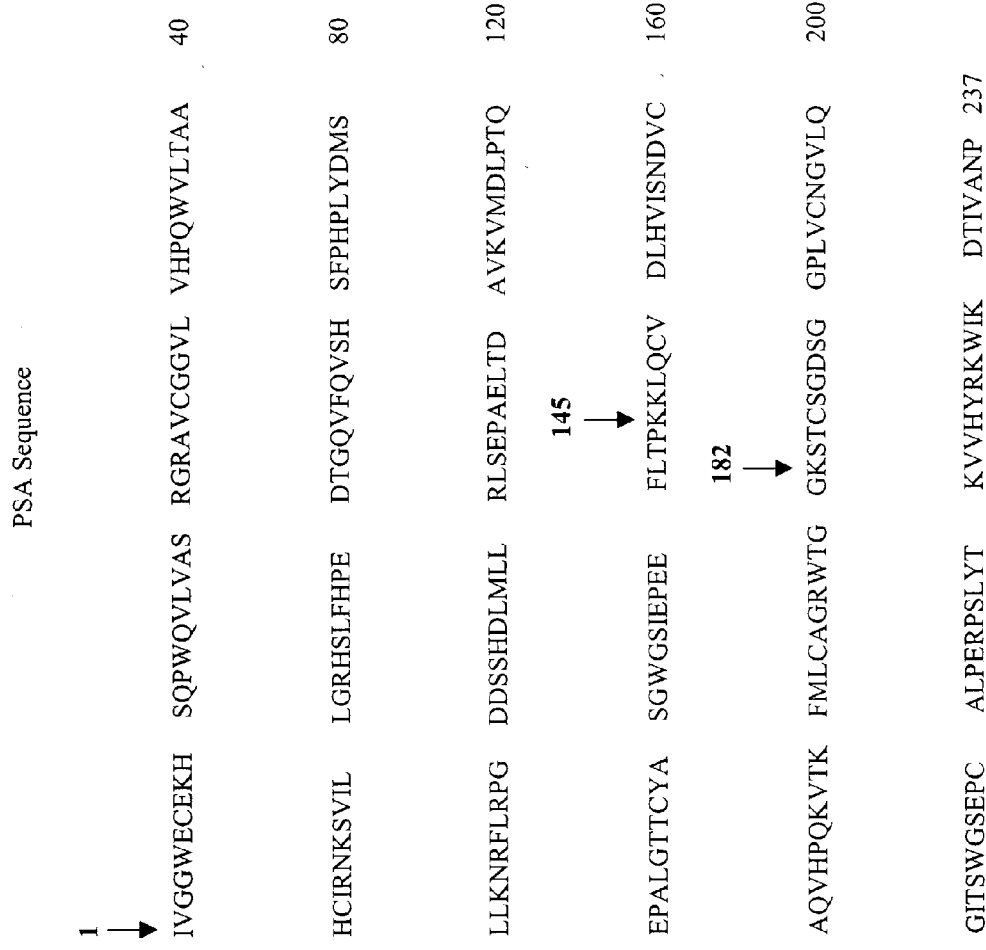
FIG. 16 shows the full amino acid sequence of mature PSA.

Another form of free PSA is BPSA. The term "BPSA" as used herein refers to a form of PSA that comprises at least one clip at Lys 182 of the amino acid sequence of a mature form of PSA. A mature form of PSA has 237 amino acid residues with a molecular mass of 28,400 D [19] and the amino acid sequence is fully described in references [20]. The sequence of the matured form of PSA is shown in FIG. 16. A BPSA of the present invention has at least one clip at Lysine 182 of the amino acid sequence of a mature form of PSA. In other words, a BPSA of the present invention has the same amino acid sequence of a mature form of PSA, except that the polypeptide chain of the PSA of the present invention has been hydrolyzed between residues 182 and 183. A BPSA of the present invention may also include an additional one or more clips at Ile 1, Lys145 and Lys146 of the amino acid sequence of a mature PSA. In one embodiment of the present invention, a BPSA of the present invention consists of two clips at Lys145 and Lys182.

The BPSA is inactive, i.e., it lacks chymotrypsin-like enzymatic activity and therefore is present in serum as free PSA, not as a PSA antichymotrypsin complex. The detailed description of BPSA and methods of producing and detecting BPSA are discussed in a co-pending U.S. Patent Application entitled "NOVEL FORMS OF PROSTATE-SPECIFIC ANTIGEN (PSA) SPECIFIC FOR BENIGN PROSTATIC HYPERPLASIA (BPH) AND METHODS OF USING SUCH," Ser. No. 09/303,208, filed on Apr. 30, 1999, the relevant contents of which are incorporated herein in their entirety.

The term "inPSA" as used herein includes all forms of free PSA that are not pPSA and BPSA. InPSA is a form of enzymatically inactive free PSA. It denotes an intact ~30 kDa, non-native form of PSA. Since internally clipped PSA remains intact under native conditions due to internal disulfide bonds, this refers to PSA that retains a molecular mass of ~30 kDa, and does not form fragment peptides under reduced denaturing conditions, such as SDS-polyacrylamide electrophoresis with 2-mercaptoethanol. This form of PSA may include enzymatically inactive PSA due to structural or conformational differences caused by misfolding, malformation of internal disulfide bonds, side-group acylation, or other factors affecting its secondary or tertiary structure. The inPSA of the present invention may not include any detectable levels of pPSA or BPSA forms by known immunoassays as described herein, but may include minor levels (<10%) of PSA with internal peptide bond cleavages other than at Lysine182, and may include any percentage of PSA that has no more than 20 amino acids removed from the N-terminus or C-terminus. Thus, the inPSA of the present invention is substantially comprised of intact, non-native PSA that does not include BPSA and pPSA. Therefore, for the purpose of the present invention, inPSA is equal to free PSA minus BPSA and pPSA.

The term "pPSA" without any prefix always means the sum of [-2]pPSA, [-4]pPSA and [-5,-7]pPSA where, "pPSA" is indicated in a mathematical equation with BPSA or inPSA.

The present invention is based on the unexpected discovery that the measurement of inPSA in serum provides improved cancer predictive value. In addition, various mathematical combinations of inPSA with total PSA, free PSA, and the other individual forms of free PSA, BPSA and pPSA, also improve the detection of prostate cancer over total PSA. This includes, but is not limited to, the level of inPSA minus pPSA, or inPSA divided by pPSA. pPSA indicates the combination of all native and truncated forms of pPSA. However, when specified, there may also be ratios of inPSA with the individual native or truncated pPSA forms, [-2]pPSA, [-4]pPSA, [-5]pPSA, and [-7]pPSA ([-5]pPSA plus [-7]pPSA may be indicated as [-5,-7]pPSA since the assay for [-7]pPSA also recognizes [-5]pPSA). In addition to inPSA, this includes mathematical relationships between BPSA and pPSA, such as BPSA minus pPSA. This invention describes a mutual and interactive relationship between inPSA, BPSA and pPSA that is non-linear and non-obvious, but which has been demonstrated experimentally to improve the detection of prostate cancer. Thus, the present invention provides a means to aid in the detection of prostate cancer by determining the levels of inPSA, pPSA and BPSA, and particularly by ratios or subtractive/additive products of inPSA with BPSA and pPSA.

Accordingly, one aspect of the present invention provides a method to aid in distinguishing prostate cancer from benign disease in a subject. The method comprises the steps of:

a) determining the amount of total PSA contained in a biological sample from the subject;

b) determining the amount of free PSA in the sample, and calculating the ratio of the free PSA to the total PSA;

c) determining the amount of inPSA in the sample; and d) correlating the amount of inPSA, or a mathematical combination of inPSA with BPSA or pPSA, contained in the sample to the presence of prostate cancer in the subject by comparing the amount of inPSA, or a mathematical combination of inPSA with BPSA or pPSA, to a predetermined value established with control samples of known cancer and benign disease diagnosis, based on both the level of total PSA and the ratio of the free PSA to the total PSA.

Methods of measuring total PSA and free PSA are well known in the art, and therefore will not be repeated herein.

The amount of inPSA may be determined by any methods described herein or known in the art, or later developed, as long as they are capable of determining the concentration of the free PSA that is not BPSA or pPSA. For example, inPSA may be measured directly or indirectly. In accordance with one embodiment of the present invention, inPSA may be measured by a method including a step of adding to a sample a sufficient amount of antibodies for BPSA or pPSA to block BPSA and pPSA contained in the sample, and measuring the amount of free PSA, which is equal to the amount of inPSA. For the purpose of the present invention, the amount of antibodies is sufficient if they can bind all of the respective BPSA or pPSA contained in the sample, and block the binding of the BPSA and pPSA with antibodies for free PSA. BPSA or pPSA is blocked if they cannot bind to an antibody for free PSA.

In accordance with another embodiment of the present invention, inPSA contained in a sample may be calculated by subtracting the amount of BPSA and pPSA from the amount of free PSA contained in a sample. The method requires the measurement of the amount of free PSA, pPSA and BPSA contained in a sample, respectively. The values for BPSA and pPSA are then subtracted from free PSA to determine the amount of inPSA.

In accordance with embodiments of the present invention, pPSA or BPSA or free PSA may be measured by immunoassays and used to calculate inPSA. Free PSA assays are commercially available and are well known in the art. Antibodies and immunoassays that may be used for measuring the amount of pPSA are described in the co-pending U.S. application Ser. Nos. 09/251,686, 09/302,965, 09/792,692; and 09/792,534, the contents of which are incorporated herein in their entirety by reference. Antibodies and immunoassays that may be used for measuring the amount of BPSA are described in a recently issued patent from U.S. application Ser. No. 09/303,208, the content of which is incorporated herein in its entirety by reference. Antibodies and immunoassays that may be used for measuring the amount of BPSA and pPSA, and methods of using these measurements in a ratio to each other to detect prostate cancer are described in recently issued patent from U.S. application Ser. No. 09/303,339, the content of which is incorporated herein in its entirety by reference.

In accordance with one embodiment of the present invention, a method for calculating the amount of inPSA contained in a biological sample may include the steps of contacting an antibody that specifically binds to the PSA of interest with the sample under a condition that allows a formation of a binary complex comprising the PSA and the antibody; (b) detecting and determining the amount of the complex; and (c) determining the amount of inPSA by subtracting the amount of pPSA and BPSA from the amount of free PSA.

For the purpose of the present invention, any agents that are capable of forming a detectable complex with pPSA, BPSA, or freePSA would be considered as equivalents of the antibody. Examples of potential molecular species include, but are not limited to, antibodies, antigen-binding fragments derived from antibodies, and equivalents of antibodies, such as, but not limited to, aptamers, etc. For the purpose of the present invention, an agent specific for pPSA or BPSA or free PSA may be selected by methods known in the art. For example, any known binding assays may be used to determine the specific binding activity of any given agent.

Typically, qualitative and/or quantitative determinations of any form of PSA required to calculate inPSA of the present invention in a sample may be accomplished by competitive or non-competitive immunoassay procedures in either a direct or indirect format. Examples of such immunoassays are the radioimmunoassay (RIA) and the sandwich (immunometric) assay. The detection of the antigens using the monoclonal antibodies of the present invention can be done utilizing immunoassays which are run in either the forward, reverse, or simultaneous modes, including immunohistochemical assays on physiological samples. Those skilled in the art will know, or can readily discern, other immunoassay formats without undue experimentation.

The terms "immunometric assay" or "sandwich immunoassay" include a simultaneous sandwich, forward sandwich, and reverse sandwich immunoassay. These terms are well understood by those skilled in the art. Those skilled in the art will also appreciate that antibodies according to the present invention will be useful in other variations and forms of assays which are presently known or which may be developed in the future. These are intended to be included within the scope of the present invention.

For the purpose of the present invention, the biological sample can be any human physiological fluid sample that contains inPSA of the present invention. Examples of the human physiological fluid sample include, but are not limited to, serum, seminal fluid, urine, and plasma, although serum and plasma is preferred. In addition, both monoclonal antibodies and polyclonal antibodies may be used as long as such antibodies possess the requisite specificity for the antigen provided by the present invention. Preferably, monoclonal antibodies are used.

In accordance with the embodiment of the present invention, the immunoassays include assays specific for [-2]pPSA, [-4]pPSA, and [-5,-7]pPSA. For example, the specific forms of pPSA are measured in the serum of men with known prostate cancer or BPH, and the levels of these analytes are used to develop algorithms with inPSA to distinguish prostate cancer from benign prostatic disease. The assays of the present invention may be used to aid in distinguishing prostate cancer from benign prostatic hyperplasia.

It is a surprise discovery of the present invention that inPSA has a significantly elevated cancer predictive value when analyzing serum specimens containing 2–10 ng/ml total PSA. In addition, various mathematical algorithms of inPSA with the other forms of total PSA, free PSA, BPSA, and pPSA also improve the detection of prostate cancer. For the purpose of the present invention, the term "mathematical combination" refers to, but is not limited to, addition, subtraction, division, and a combination thereof. For example, a mathematical combination may include the level of inPSA minus PPSA, or inPSA divided by PPSA. PPSA, in this case, may be the combination of all native and truncated forms of pPSA, or the individual [-2], [-4], and [-5,-7]pPSA forms. In addition to inPSA, this includes mathematical relationships between BPSA and pPSA, such as BPSA minus pPSA. This invention describes a non-linear and non-obvious relationship between the 3 individual forms of free PSA that make up total free PSA, i.e., inPSA, BPSA, and pPSA. This relationship was discovered experimentally. Thus, the present invention provides a means to aid in the detection of prostate cancer by determining the levels of inPSA, pPSA, and BPSA, and particularly by ratios or subtractive products of inPSA with BPSA and pPSA.

The inPSA divided by PPSA and inPSA minus pPSA also have a significantly elevated cancer predictive value within specific subpopulations of total PSA that have highly elevated % free PSA. The relationship between inPSA and pPSA improves the detection of cancer in men with % free PSA greater than 20%, and particularly greater than 25%.

According to the embodiments of the present invention, the total PSA may be at any concentration below 20 ng/ml, or more preferably below 10 ng/ml, or most preferably in the range of 2.5 to 10 ng/ml. In one preferred embodiment of the invention, the total PSA is between 2.5 and 4 ng/ml. In another preferred embodiment, the total PSA is in the range 4–10 ng/ml. The ratio of free PSA to total PSA may be any range of free PSA that is typically found in patient sera, from 1% to 50%, though in one embodiment of the invention, the preferred range of free PSA is greater than 20%, and most preferably, greater than 25%. In a particular embodiment, the total PSA is in the range of 4 to 10 ng/ml, and the ratio of free PSA is in the range of greater than 20%, or 25%. The pPSA may be [-2]pPSA, [-4]pPSA, [-5,-7]pPSA, or the combined sum of these three forms of native and truncated pPSA, indicated as pPSA. The inPSA may be preferably expressed as ng/ml inPSA in the serum, as inPSA divided by pPSA, or inPSA minus pPSA. The sample may be any physiological fluid, though serum or plasma is preferred.

For the purpose of the present invention, the amount of inPSA alone and in combination with total and free PSA, pPSA and BPSA detected in a sample of a patient may be correlated to the presence of prostate cancer in any way that generates diagnostic value for determining the presence of prostate cancer. In accordance with embodiments of the present invention, the amount of inPSA, or a mathematic combination with total PSA, free PSA, BPSA or PPSA, is compared to a predetermined value for determining the presence of prostate cancer. In view of the teaching of the present invention, one skilled in the art through routine experimentation can readily determine the "predetermined cut off value" (or threshold) or other analytical parameters necessary to allow the use of the level of the inPSA in determining the presence of prostate cancer. For example, one may compare the above-discussed ratio of inPSA in individuals diagnosed with prostate cancer with individuals that do not have prostate cancer or have BPH to determine the cut off values. Receiver Operating Characteristic (ROC) analysis can be used to determine a cut off value with required specificity and sensitivity. ROC analysis is known in the art and is described in detail in reference 22 (22), the relevant content of which is incorporated herein by reference. Then, the mathematic combination or the amount of inPSA of a sample may be compared to the pre-determined cut off value for determining the presence of prostate cancer in a subject, as determined from the ROC analysis, wherein a higher or lower level of inPSA or mathematical combination of inPSA with other PSA forms may be an indication of prostate cancer. One skilled in the art would be able to determine, based on the ROC analysis, whether the higher level or the lower level is an indication of prostate cancer in view of the teaching of the present invention. This and other methods of determining the cutoff value with required specificity and sensitivity are well known in the art and need not be repeated (23–29).

The invention is further described by reference to the following examples.

EXAMPLE I

Analysis of Serum of Men with Cancer and Benign Disease Containing Total PSA Between 4 and 10 ng/ml Materials and Methods Development of Monoclonal Antibodies (mAbs) to BPSA and pPSA Monoclonal antibodies to [−2]pPSA, [−4]pPSA, [−5,−7] pPSA, and BPSA have been previously described[12–16]. The [−7]pPSA mAb also recognizes the [−5]pPSA form of pPSA. For the purposes of these examples, wherever the term [−7]pPSA is written, both [−5] plus [−7]pPSA is indicated. The term pPSA indicates [−2] plus [−4] plus [−5] plus [−7]pPSA.

Immunoassay of PSA

The concentration of PSA in serum and purified preparations was determined by Tandem®-MP PSA and Tandem®-MP free PSA assays (Hybritech Incorporated, San Diego, Calif.; Beckman Coulter, Inc., Fullerton, Calif.).

Immunoassay of [−2], [−4] and [−5,−7] pPSA

The immunoassay we have developed for the measurement of the pPSA forms is as follows. 50 ul of biotinylated anti-PSA Ab PSM 773 at 5 ug/ml in Tandem® PSA zero cal diluent is added to a EG&G Wallac streptavidin coated microplate and allowed to react at room temperature for 1 hour with shaking. The plate is then washed 5 times with Tandem® E wash. 50 ul of Tandem® PSA zero cal diluent is then added to the plate followed by 50 ul of sera or antigen to be tested. The mixture is allowed to react at room temperature for 2 hours as above. The plate is then washed 5 times with Tandem® E wash. 100 ul of a ImA solution of the appropriate Europeum-labelled detect mAb for the intended measurement of each form of pPSA is added to the plate. For [−2]pPSA, this is PS2X373; for [−4]pPSA, PS2V 411; and for [−5,−7]pPSA, this is PS2P309. The mixture is allowed to react at room temperature for 1 hour as above. The plate is then washed 5 times with Tandem® E wash and read on a EG&G Wallac Victor instrument.

Immunoassay of BPSA

The BPSA assay protocol is as follows. Biotinylated capture anti-PSA mAb, PSM773 (100 uL, 0.25 mg/L) was incubated for 1 hour with shaking in a streptavidin microtiter plate. The plate was washed with blocking buffer (50 uL), followed by adding 50 uL of either the calibrator or sample, and allowed to incubate with shaking for 2 hour. The plate was washed and the alkaline phosphatase-labeled anti-BPSA mAb, PS2E290 was added (100 uL, 2 ug/ml) and allowed to incubate with shaking for 1 hour. The plate was washed and 100 uL of 4-methylumbelliferyl phosphate added and allowed to incubate shaking for 5 minutes. The plates were then read at 5, 60 and 120 minutes. Relative fluorescence was measured in a 1234 Delfia research fluorometer (Wallac, EG&G).

Receiver Operating Characteristic (ROC) Curve Analysis

ROC analysis and graphs were generated using the MedCalc software program (MedCalc Software, Belgium, (info@medcalc.be)). The theory and practice is described in: Zwieg and Campbell, Receiver-operating characteristic (ROC): a fundamental evaluation tool in clinical medicine, *Clinical Chemistry,* 39, 561–577, 1993.

Results

Figure 1:
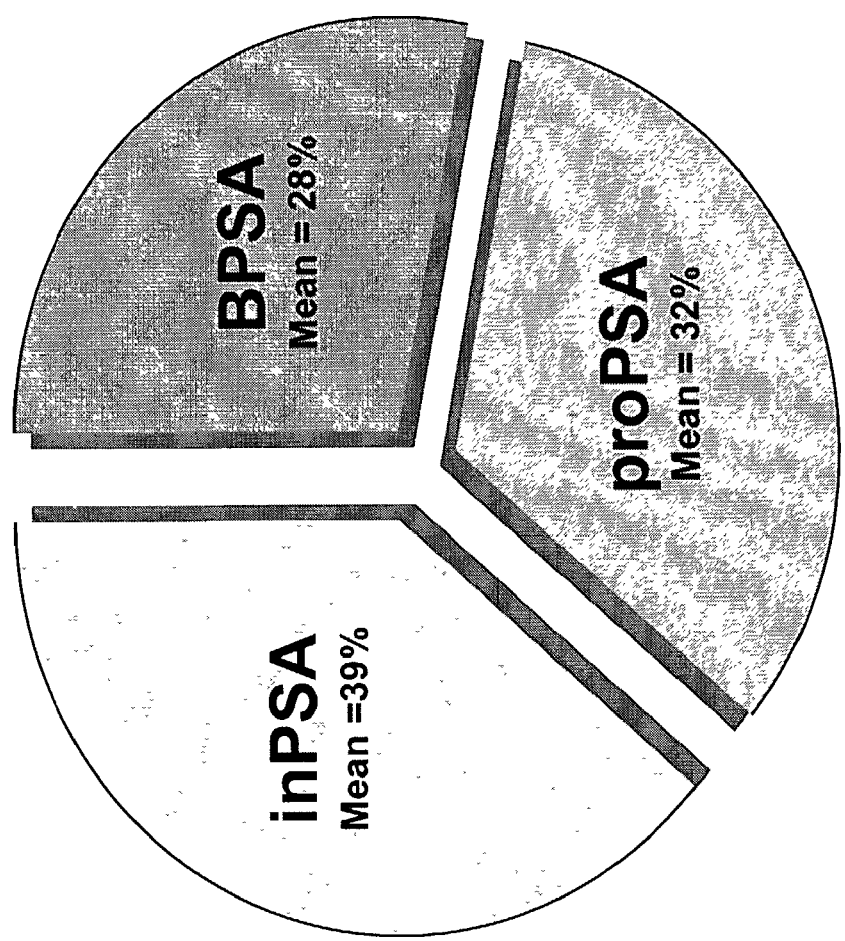
FIG. 1 shows the typical proportions of pPSA, BPSA and inPSA in cancer serum.

The typical mean proportions of the individual free PSA forms, BPSA, pPSA and inPSA in cancer serum with total PSA 4–10 ng/ml are shown in FIG. 1. Individual pSPA and BPSA samples can range from 0 to greater than 70% of the free PSA. This demonstrates that the individual free PSA forms can each represent significant and variable percentages of the free PSA, and supports data that indicates that inPSA alone and in combination with BPSA and pPSA represents unique serum profiles that can improve the detection of cancer serum. The ROC curves and analyses were performed on approximately 1100 serum samples with the diagnosis of cancer or benign disease, with total PSA in the range of 2 to 10 ng/ml. Free PSA values were measured for each sample. BPSA and the individual pPSA forms, [−2] pPSA, [−4]pPSA, and [−5,−7]pPSA were measured in each sample. Unless otherwise indicated, pPSA indicates the sum of all three pPSA forms. The inPSA/was calculated as free PSA minus BPSA and pPSA The values for each PSA isoform were entered into the MedCalc program in order to generate an ROC curve analysis. ROC is a statistical method to assign a positive and negative predictive value of cancer for each sample in the cohort and is the most widely used method to assess the value and performance of PSA and free PSA assays as predictors of cancer. In the simplest of terms, the area under the curve, AUC, for each ROC analysis is used to assess assay predictive value. A higher AUC value indicates a better overall predictive value. ROC values range from 0.5 (no improvement over random chance) to 1.0 (a perfect assay with 100% predictive value). Internal labeling of the ROC curves is as follows: T=total PSA, F=free PSA, i=inPSA; B=BPSA; P=PPSA; 2p=[−2]pPSA. For example, in the equation, (i−P)/T equals inPSA minus pPSA divided by total PSA.

In most cases, the objective of the ROC analysis is to maximize the discrimination of men with cancer and to minimize biopsies on those men who do not have cancer, i.e., false positives. When analyzing biological samples such as PSA in serum, there is a balance between the detection of true positives and false positives. For example, depending on the desired outcome, it may be most desirable to detect 95% of the cancers, and this is inevitably accompanied by a higher false positive rate for those men with the benign disease. In the case of % free PSA, for example, in order to detect 95% of the cancers, it requires biopsies of all men who have less than 25% free PSA. This is, however, accompanied by an 80% false positive rate. These hypothetical examples are meant to illustrate that the assessment and value of the ROC analysis is not absolute, and in the case of the current invention with inPSA, will require routine experimentation to establish the exact parameters to be used in practice. However, in view of the teaching of the present invention, one skilled in the art should be able to readily determine the necessary parameters without undue experimentation. Examples given below are meant to demonstrate the value and efficacy of inPSA, inPSA in combination with pPSA and BPSA, and pPSA in combination with BPSA in detecting cancer in a given population, and under a given set of criteria, but the uses and cut offs for these parameters are not limited to these examples.

Figure 2:
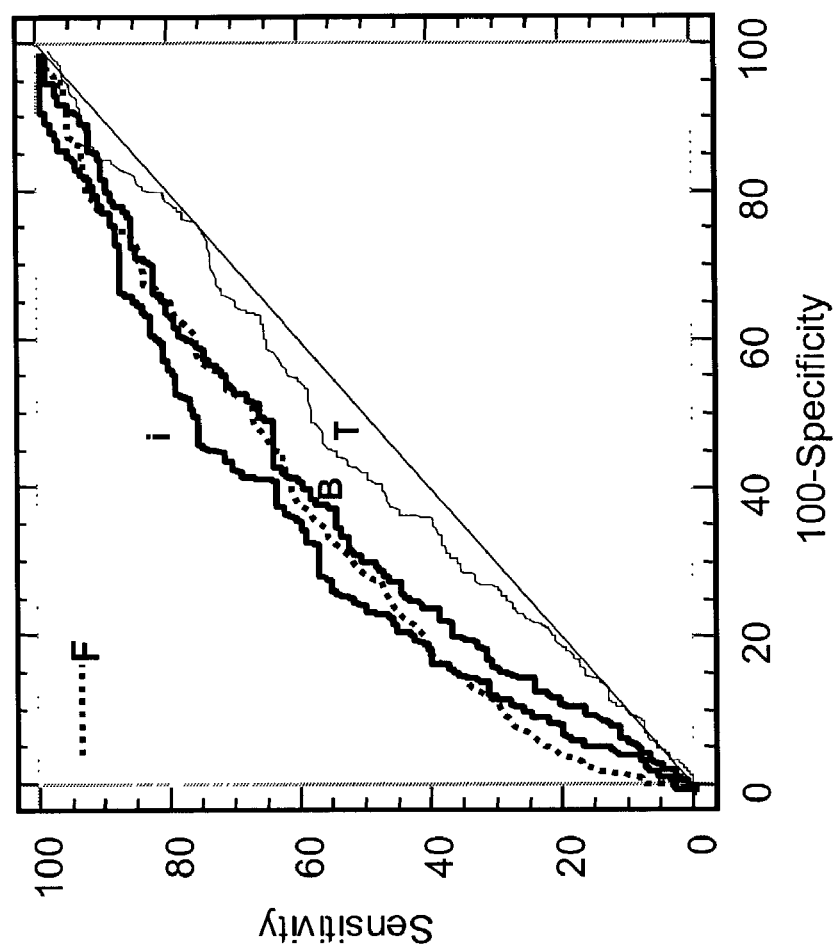
FIG. 2 shows the Receiver Operating Characteristic (ROC) analysis overlay comparing free PSA; F, total PSA, T; inPSA, i; and BPSA, B in men with cancer or BPH and 4–10 ng/ml total serum PSA
Figure 3:
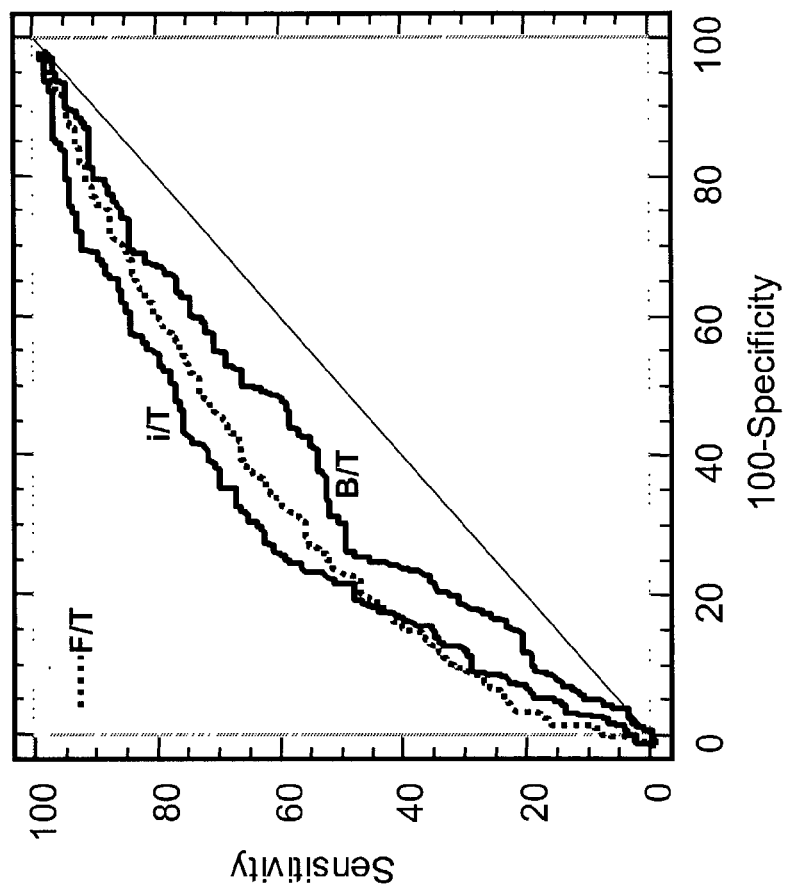
FIG. 3 shows the ROC analysis of free/total PSA, inPSA/total PSA, and BPSA/total PSA in men with cancer or BPH and 4–10 ng/ml total serum PSA.
Figure 4:
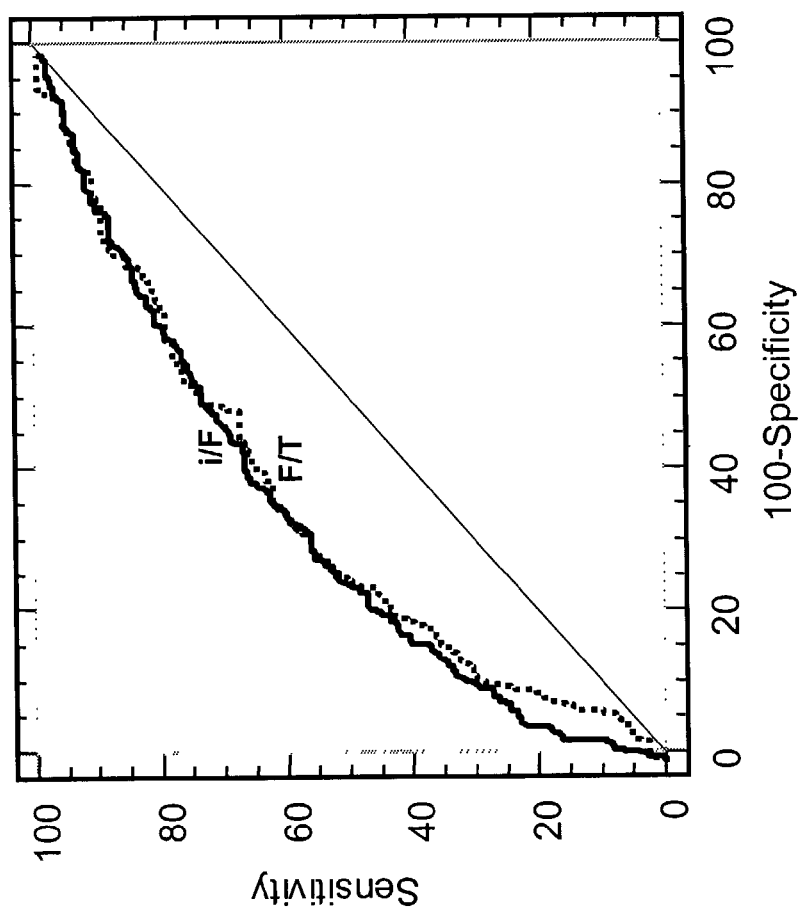
FIG. 4 shows the ROC analysis inPSA/free PSA and free PSA/total PSA in men with cancer or BPH and 4–10 ng/ml total serum PSA.

FIG. 2 shows an overlay of ROC curves for total PSA, inPSA, BPSA and Free PSA expressed as ng/ml in serum. inPSA has the highest area under the curve (AUC) which indicates that inPSA discriminates cancer from benign better than the other parameters. In the field of PSA testing, it is known that the % free PSA improves cancer detection compared to total PSA alone in the early cancer detection range of 4–10 ng/ml total PSA. The % free PSA, i.e., F/T, has been demonstrated to be the best diagnostic PSA test for cancer and is considered the standard by which one judges new tests. FIG. 3 shows that %inPSA (inPSA/total PSA) is superior to % free PSA. FIG. 4 shows that inPSA as a ratio with free PSA is comparable to free PSA expressed as a ratio with the total PSA. These examples show that inPSA and inPSA as a ratio with the free or total PSA gives superior cancer detection compared to total or free PSA alone.

Figure 5:
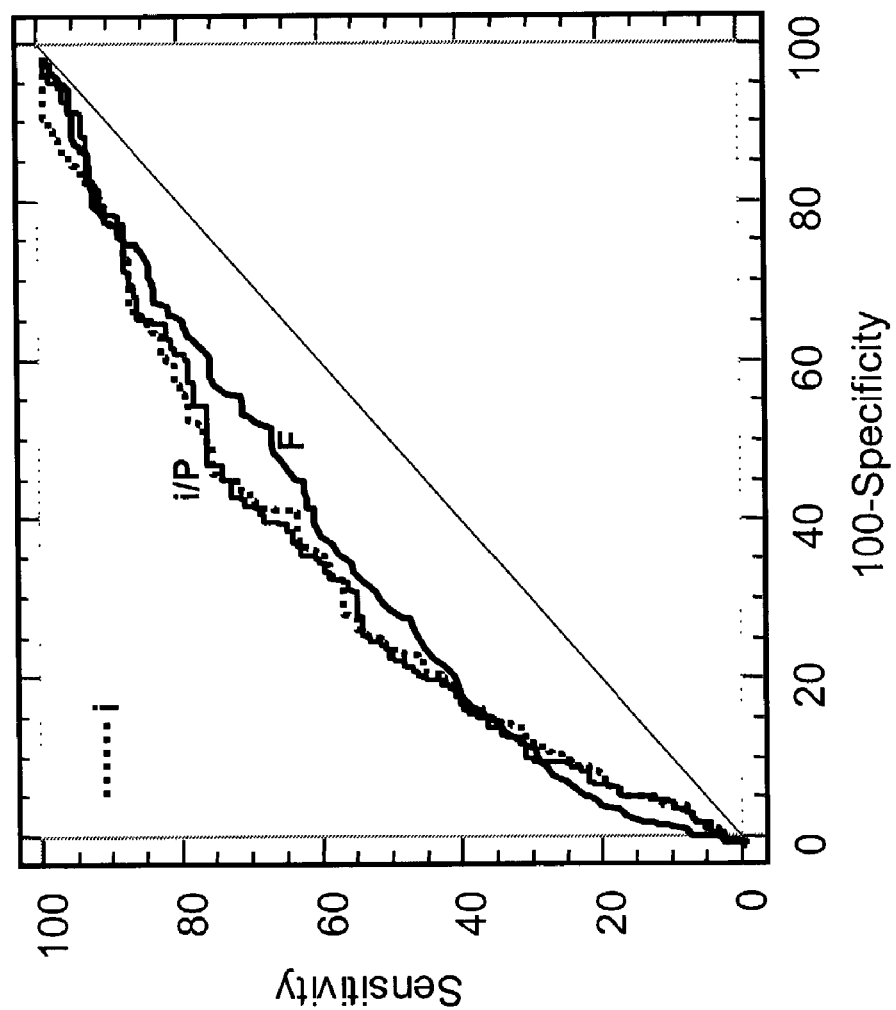
FIG. 5 shows the ROC analysis of inPSA, inPSA/pPSA, and free PSA in men with cancer or BPH and 4–10 ng/ml total serum PSA.
Figure 6:
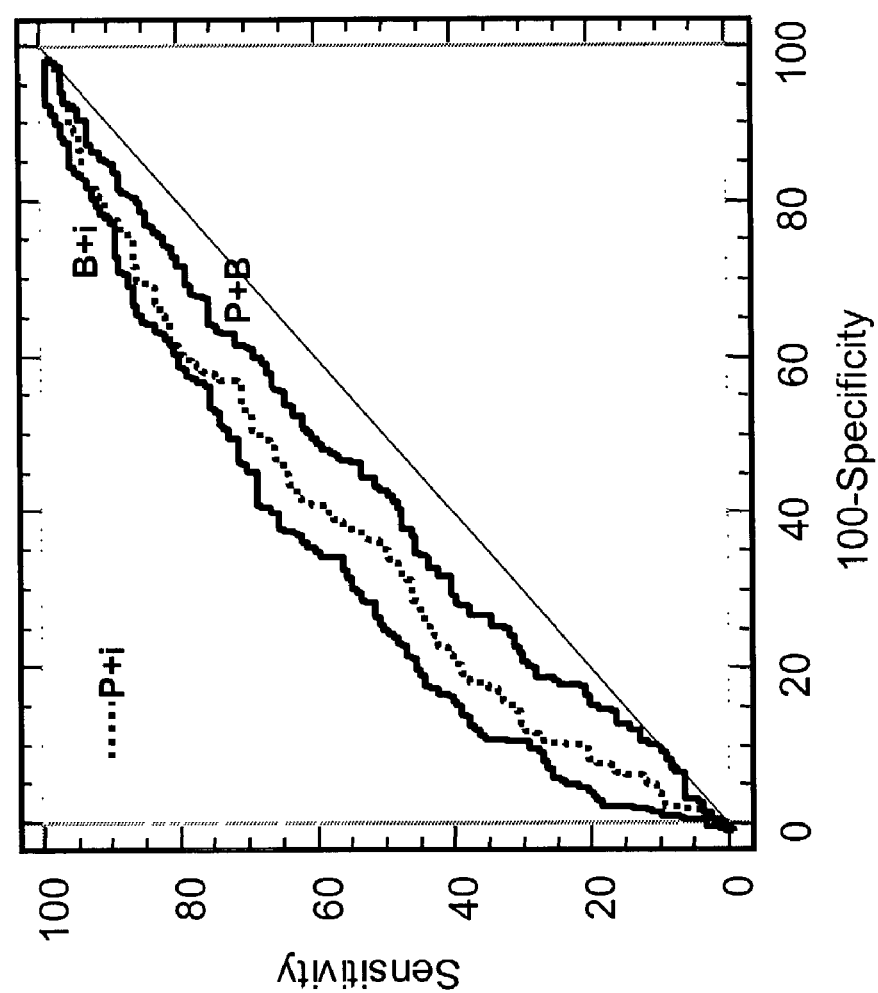
FIG. 6 shows the ROC analysis of pPSA+inPSA, pPSA+BPSA, BPSA+inPSA in men with cancer or BPH and 4–10 ng/ml total serum PSA.
Figure 7:
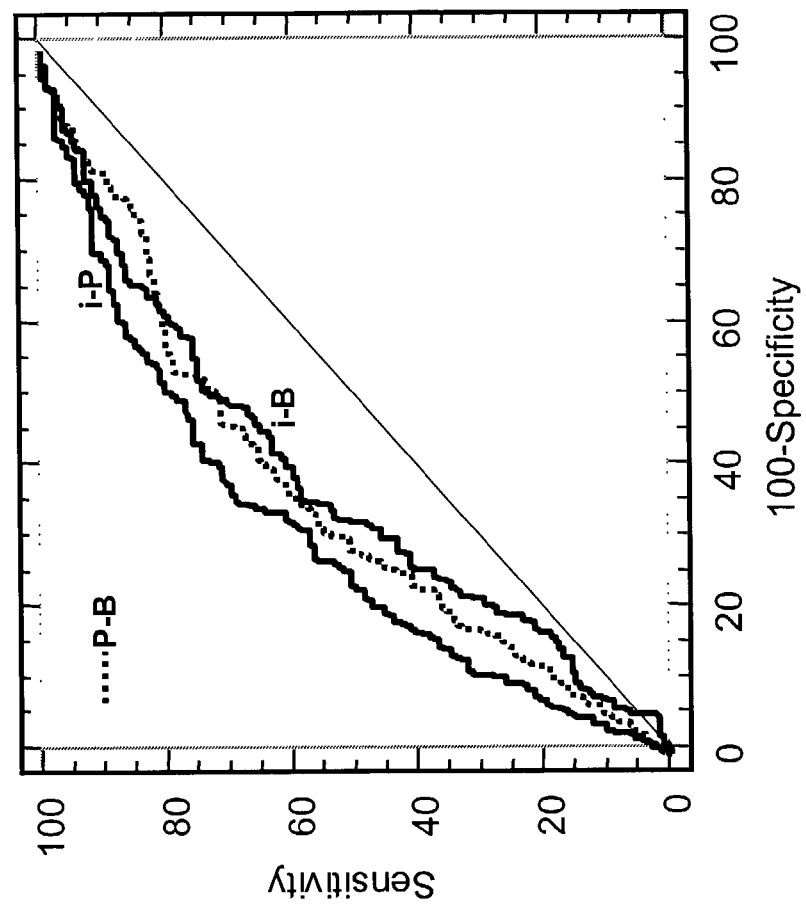
FIG. 7 shows the ROC analysis of pPSA minus BPSA, inPSA minus BPSA, and inPSA minus pPSA in men with cancer or BPH and 4–10 ng/ml total serum PSA.
Figure 8:
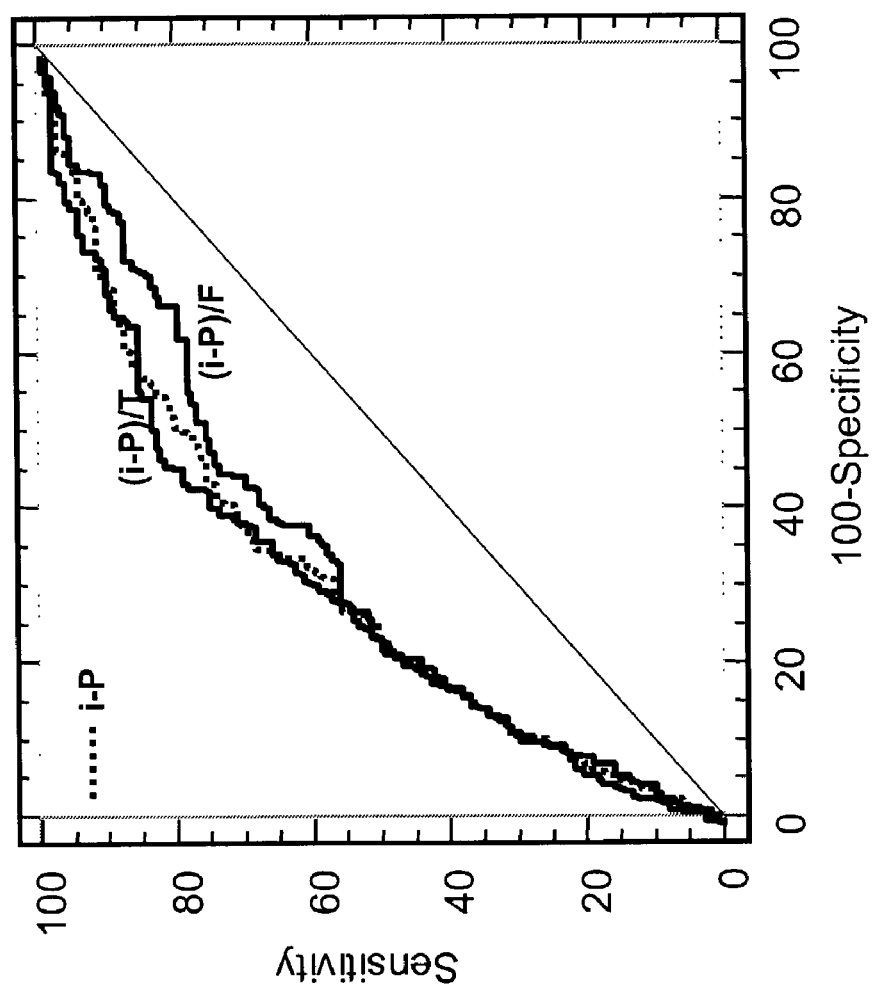
FIG. 8 shows the ROC analysis of inPSA minus pPSA, (inPSA minus pPSA)/total PSA, and (inPSA minus pPSA)/free PSA in men with cancer or BPH and 4–10 ng/ml total serum PSA.

FIGS. 5–8 show that various mathematical combinations of inPSA with other free forms of PSA can improve cancer detection even more than inPSA alone. FIG. 5 shows that inPSA/pPSA is comparable to inPSA alone, but better than free PSA. FIG. 6 shows the various possible combinations of inPSA, pPSA and BPSA with one another. BPSA plus inPSA gives the best AUC and, therefore, the best cancer detection. pPSA plus inPSA performs less well and pPSA plus BPSA performs least well amongst this combination. FIG. 7 shows the various possible combinations of pPSA, BPSA and inPSA subtracted from one another. The values obtained by these mathematical constructs cannot be deduced or measured by any of the assay methods by themselves. All give significant AUCs that improve cancer detection over free or total PSA. FIG. 8 shows various further ratios of inPSA minus pPSA with free and total PSA. Using inPSA minus PPSA as a ratio with total PSA improves the ROC over inPSA minus PPSA alone. Each of the ROC examples in FIGS. 5–8 demonstrates that the various combinations and ratios of inPSA, pPSA and BPSA provide significant AUC in the ROC analysis, and can improve cancer detection over free and total PSA alone.

Figure 9:
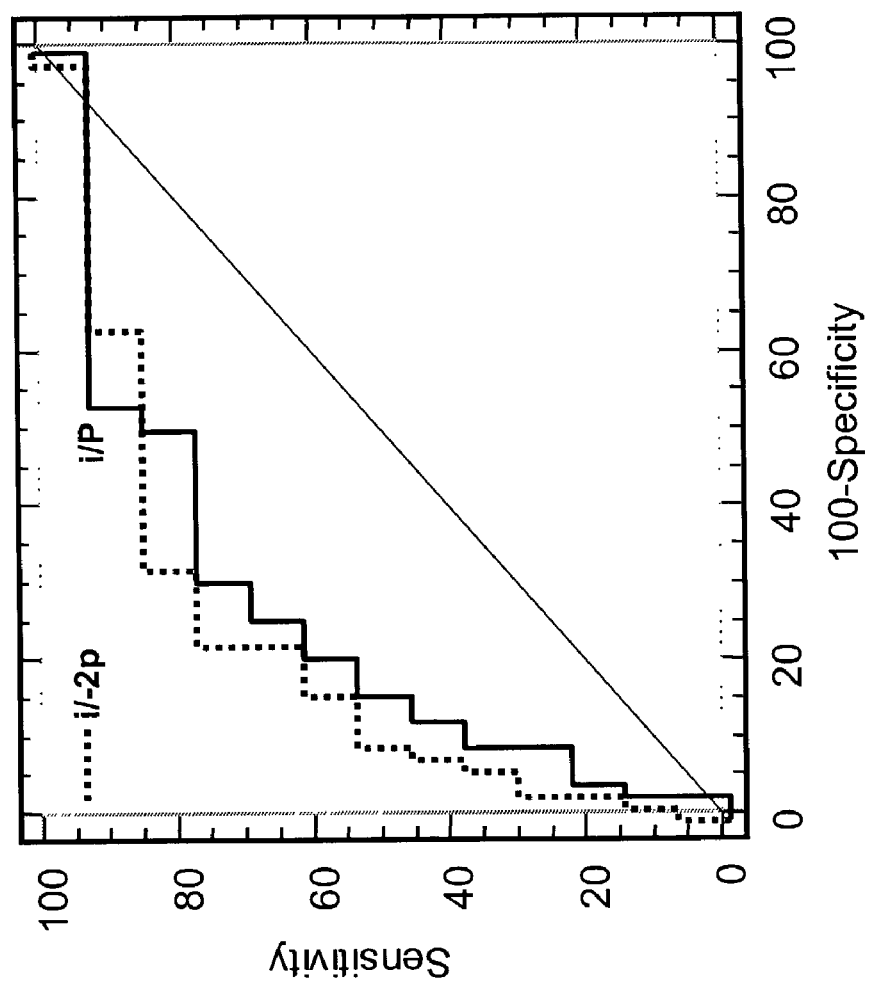
FIG. 9 shows the ROC analysis of inPSA/pPSA and inPSA/[−2]pPSA in men with cancer or BPH, 4–10 ng/ml total serum PSA and greater than 25% free PSA.

FIG. 9 shows one additional example of improved cancer detection using inPSA. In this case, we examined men with prostate cancer with elevated % free PSA. In this figure, only men with % free PSA greater than 25% were analyzed. In truly random screening populations, it is recommended that men with greater than 25% free PSA not be biopsied for cancer since the probability is only about 8% that cancer will be found. Thus, cancers in this group of men would tend to remain undetected under normal circumstances since there is no routine blood test to predict cancer in this group. FIG. 9 shows that inPSA/total PSA and inPSA/[–2]pPSA has a highly enhanced predictive value for cancer in this group. It was unanticipated that inPSA would show selective cancer prediction in a specific range or cut off of % free PSA.

EXAMPLE II

Analysis of Serum of Men with Cancer and Benign Disease Containing Total PSA Between 2.5 and 4 ng/ml As in Example I, the same series of PSA assays were measured in this cohort of patients who have total PSA values from 2.5–4 ng/ml. The range from 2.5–4 ng/ml is an area where many cancers are present but at a lower occurrence than in the 4–10 ng/ml patients in random screening populations. Total PSA does not discriminate cancer in this range, and current attempts to use % F to improve cancer detection in this range have not shown diagnostic value.

Figure 10:
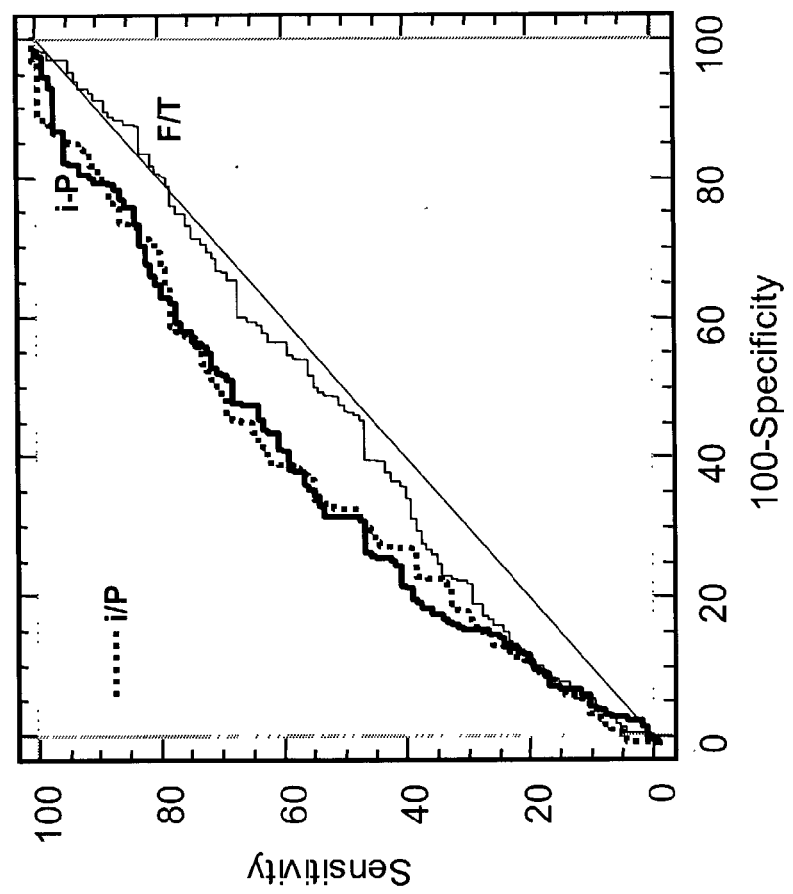
FIG. 10 shows the ROC analysis of inPSA/pPSA, inPSA minus pPSA and free PSA/total PSA in men with cancer or BPH and 2.5–4 ng/ml total serum PSA.
Figure 11:
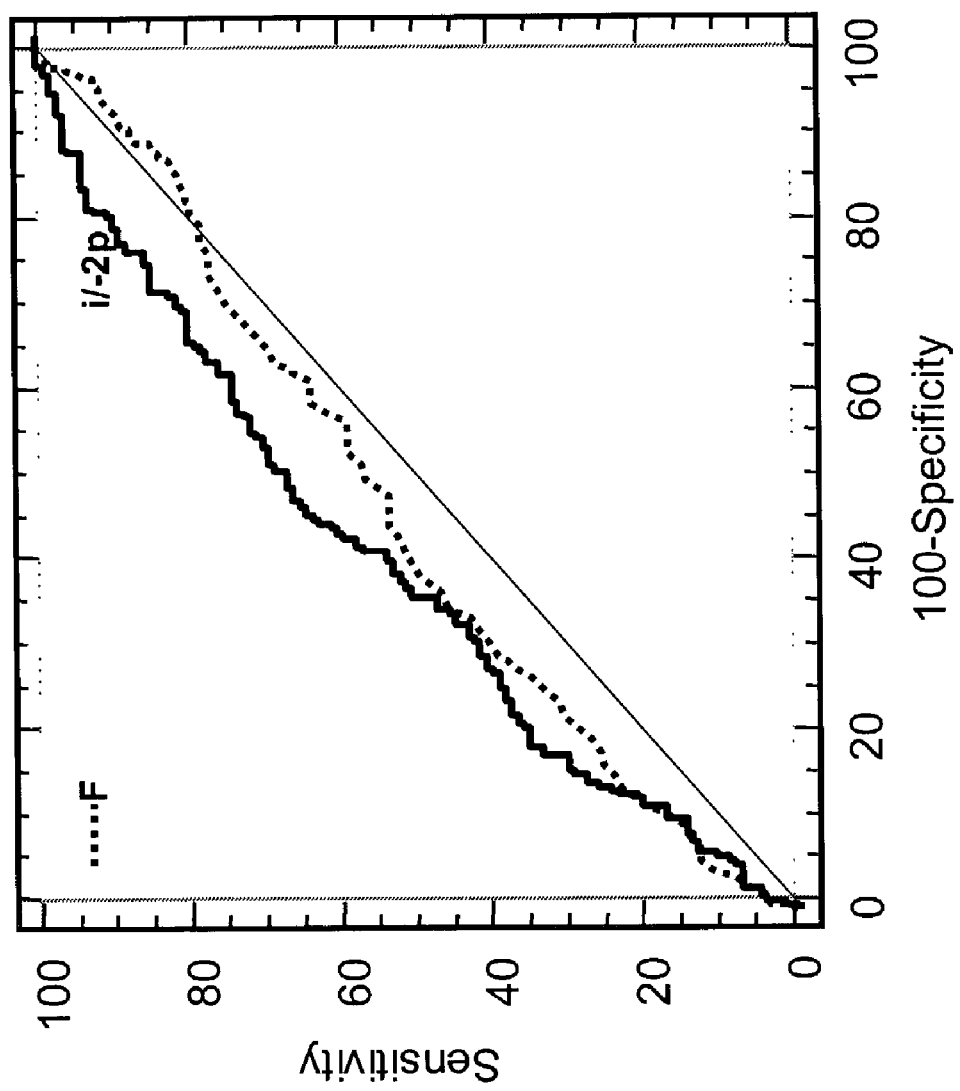
FIG. 11 shows the ROC analysis of free PSA, and inPSA/[−2]pPSA in men with cancer or BPH and 2.5–4 ng/ml total serum PSA.

FIGS. 10 and 11 show that inPSA in the range from 2.5–4 ng/ml is a much better predictor of prostate cancer than free forms of PSA. In FIG. 10, inPSA/pPSA and inPSA minus pPSA give similar AUCs which give a positive discrimination of cancer, whereas F/T give virtually no discrimination of cancer. In FIG. 11, inPSA/[–2]pPSA also gives a positive cancer discrimination whereas free PSA gives little or no cancer discrimination.

These examples show the inPSA also gives positive prostate cancer discrimination whereas the normal parameters of free and total PSA do not discriminate cancer from benign disease when the total PSA is below 4 ng/ml.

EXAMPLE III

Analysis of Serum of Men with Cancer and Benign Disease Containing Total PSA Between 2.5 and 10 ng/ml The current PSA range for the early detection of prostate cancer is 4–10 ng/ml. It is recommended that men with PSA in this range receive a biopsy to determine if cancer is present. There is discussion in the clinical literature whether to lower the PSA cutoff below 4 ng/ml, possibly to 2.5 ng/ml. In such a case the current diagnostic PSA and free PSA would be used to recommend biopsy unless other improved tests were available.

Figure 12:
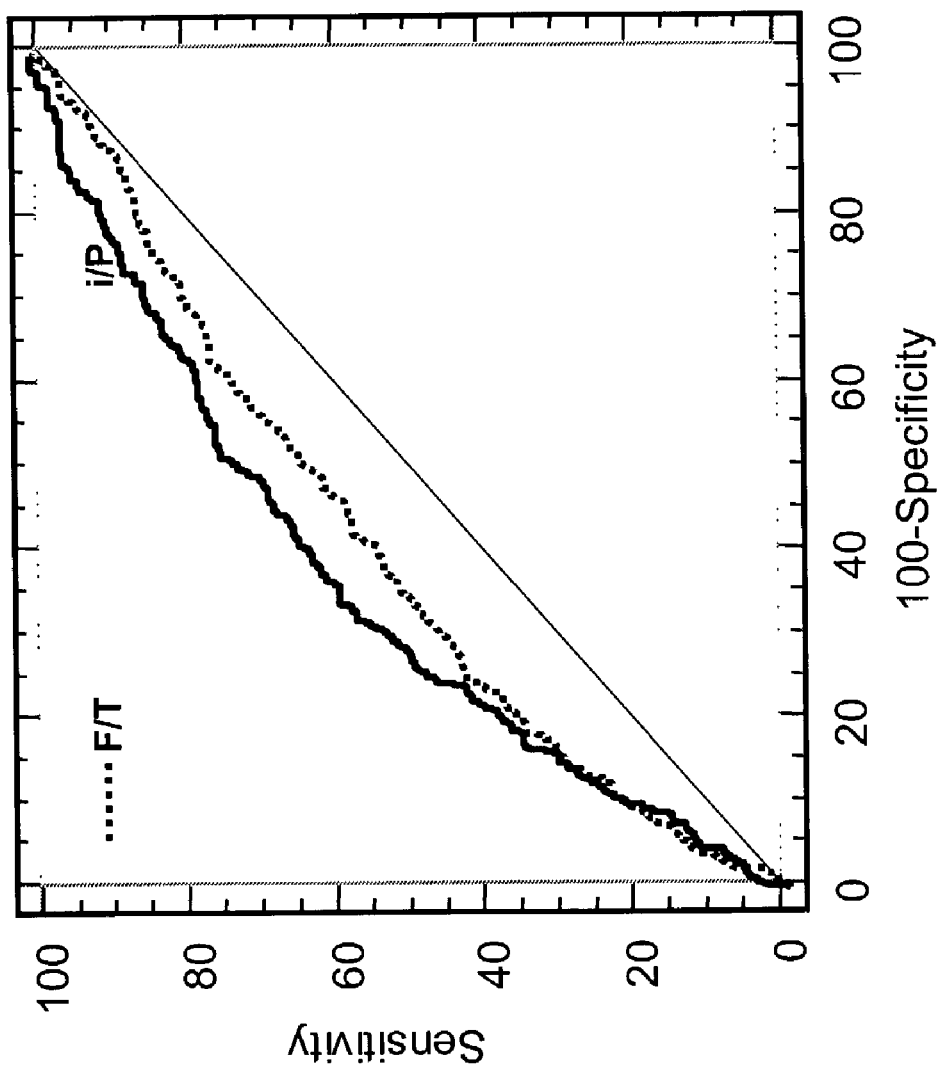
FIG. 12 shows the ROC analysis free PSA/total PSA and inPSA/pPSA in men with cancer or BPH and 2.5–10 ng/ml total serum PSA.
Figure 13:
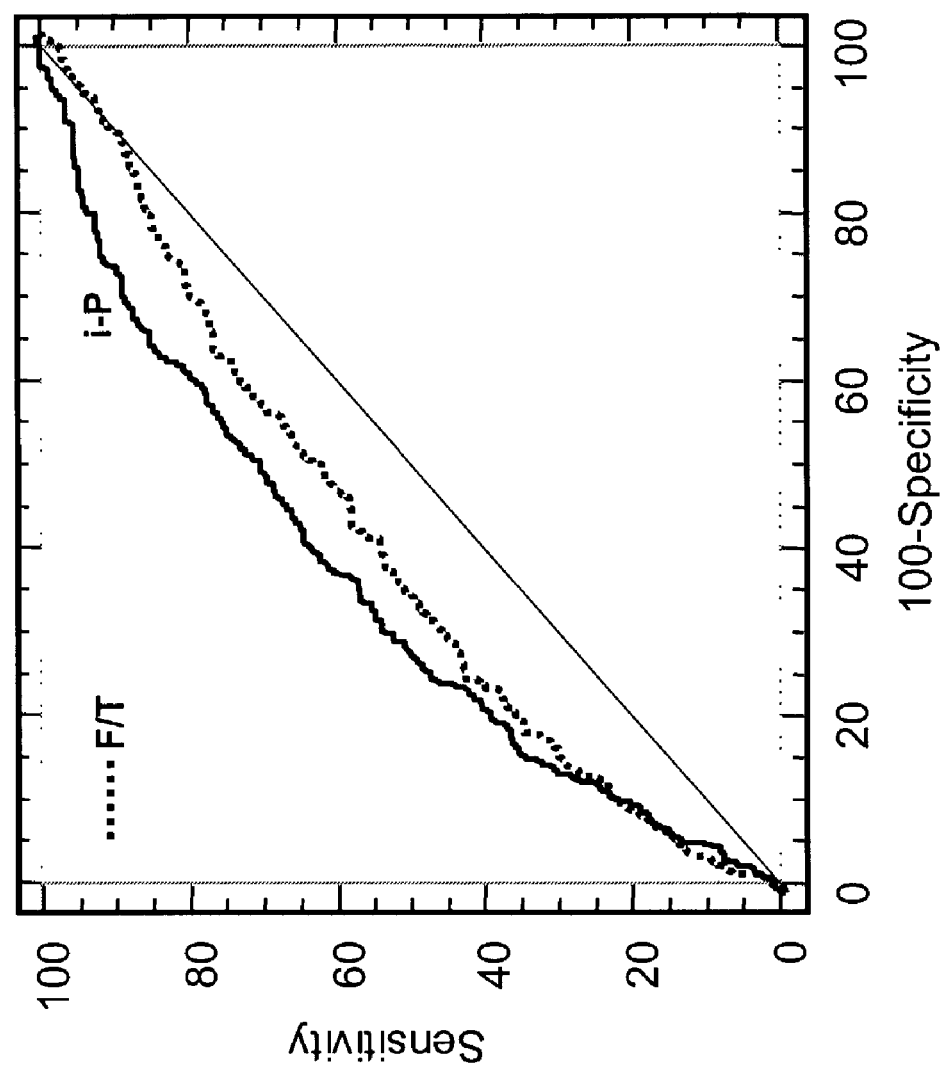
FIG. 13 shows the ROC analysis free PSA/total PSA and inPSA minus pPSA in men with cancer or BPH and 2.5–10 ng/ml total serum PSA.

FIGS. 12 and 13 inPSA can be used to improve cancer detection over current assays throughout the whole range of 2.5 to 10 ng/ml. In FIG. 12 inPSA/pPSA improves cancer detection over F/T PSA. In FIG. 13 inPSA minus pPSA give an even better improvement compared to F/T PSA. Since F/T PSA is the best PSA diagnostic marker in use today, this indicates that inPSA has significant potential for cancer discrimination.

EXAMPLE IV

Methods of Purifying inPSA and Production of inPSA Antibodies

Figure 14:
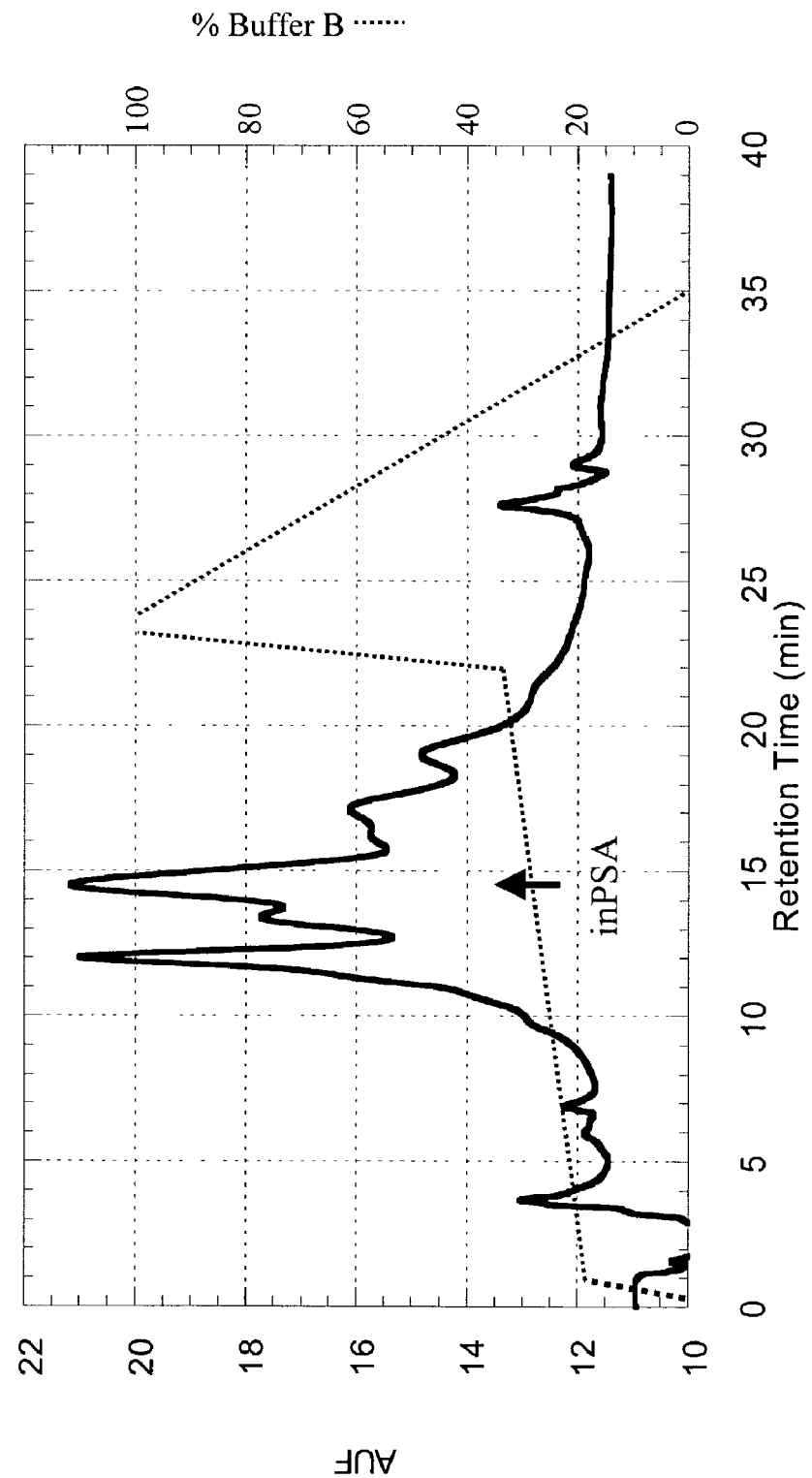
FIG. 14 shows the cation exchange chromatographic profile of all forms of inactive seminal plasma PSA
Figure 15:
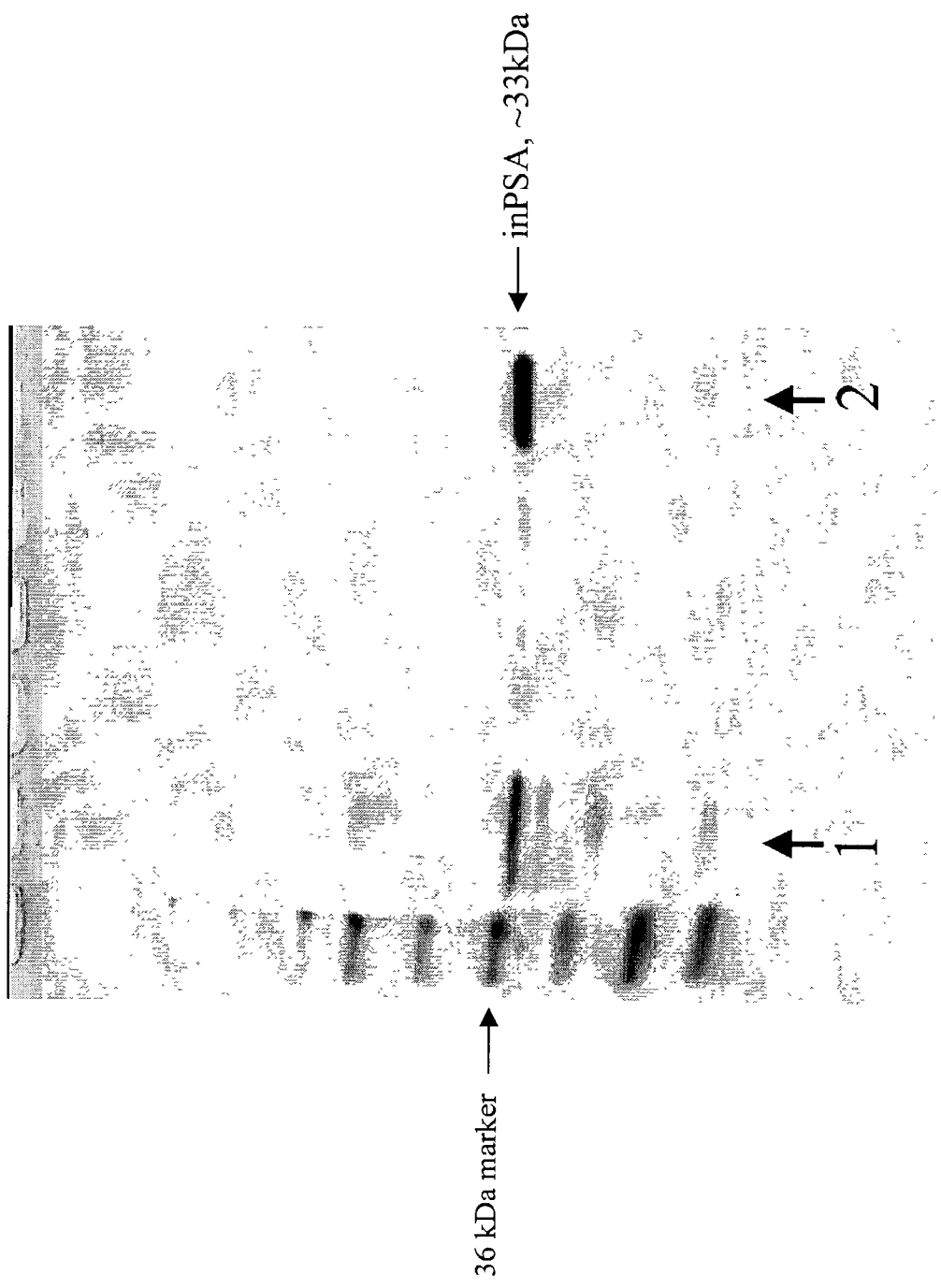
FIG. 15 shows SDS-PAGE gel under reducing conditions showing the original starting material containing all forms of inactive seminal plasma PSA, designated as lane 1, and the purified peak of inPSA shown in FIG. 14, containing purified intact, non-native PSA, indicated as lane 2.

Method I: Purifying inPSA After in vitro Incubation of Seminal Plasma with Serum Ten ml of seminal plasma was incubated with 50 ml of female serum and incubated for 3 hours at 37° C. This mixture was diluted 1:2 with PBS (phosphate buffered saline, pH 7), filtered through 0.2 micron membrane filters and applied to an immunoaffinity column containing the monoclonal mAb PSM773. PSM773 has been previously demonstrated to bind all forms of free PSA and PSA complexed to ACT. The PSA eluted from the immunoaffinity column was then applied to an S12 size exclusion column and the free PSA eluting as ~33 kDA was collected. The purified inactive PSA was dialyzed into a buffer consisting of 25 mM Mes, (2-[N-Morpholino]ethanesulfonic acid)), and 40% acetonitrile pH 5.6 (Buffer A) and applied to a 0.8×5 cm MA7S cation exchange column (Bio-Rad Laboratories, Hercules, Calif.) equilibrated in buffer A. The PSA forms were eluted with buffer B consisting of 400 mM sodium acetate, 40% acetonitrile, pH 7.0 using the gradient indicated in FIG. 14. Peaks from FIG. 14 were collected, dialyzed vs. PBS, concentrated and applied to 4–18% gradient polyacrylamide gels under reducing conditions with 2-mercaptoethanol. The proteins were stained with Commassie Blue under standard conditions.

Method II: Immunoaffinity Purification of inPSA After in vitro Incubation of Seminal Plasma with Serum Ten ml of seminal plasma is incubated with 50 ml of female serum and incubated for 3 hour at 37° C. This mixture is diluted 1:2 with PBS (phosphate buffered saline, pH 7), filtered through 0.2 u membrane filters and applied to an immunoaffinity column containing the monoclonal mAb PSM773. PSM773 has been previously demonstrated to bind all forms of free PSA and PSA complexed to ACT. The PSA eluted from the immunoaffinity column is then applied to an S12 size exclusion column and the free PSA eluting as ~33 kDA is collected. The purified inactive PSA is dialyzed vs. PBS and applied to an immunoaffinity column containing a combination of antibodies selected from the list: PS2P309, PS2P446, PS2X094, PS2X373, PS2V411, and PS2V476 to remove these pPSA forms of PSA. The flowthrough is then applied to an immunoaffinity column containing the mAbs PS2E290 and/or PS2E055 to remove BPSA from the solution. The flowthrough now contains inPSA, which is free PSA that does not contain BPSA and pPSA.

Preparation of Monoclonal Antibodies to inPSA

The purified inPSA may be injected into mice and the resultant antibodies in the ascites tested for reactivity to inPSA using standard techniques of tissue culture and screening [21]. This includes technologies of antigen tolerization and the use of anti-PSA blocking antibodies on the inPSA to minimize the response to dominant PSA epitopes. For screening purposes, the antibodies would be screened against PSA released from PSA-ACT. It is known that active, native PSA can be released from the PSA-ACT complex with a mild chemical treatment, and that this PSA appears normal in all respects with seminal plasma PSA [8]. Active PSA used to screen inPSA would select for antibodies that recognize the properties of inPSA that are different from the properties of active PSA.

DISCUSSION

These examples demonstrate that the inPSA isoforms of free PSA act as independent markers for cancer detection compared to free PSA. This is true throughout the current diagnostic PSA range of interest, 2.5–10 ng/ml. These findings with inPSA extend our current understanding of free PSA forms. We have previously shown that pPSA forms improve cancer detection in patient populations in co-pending U.S. patent application Ser. No. 09/302,965, filed on Apr. 30, 1999 (which in turn is a continuation-in-part of U.S. application Ser. No. 09/251,686, filed on Feb. 17, 1999, which in turn is a continuation of U.S. application Ser. No. 08/846,408, filed on Apr. 30, 1997). We have issued patents for BPSA (U.S. application Ser. No. 09/303,208) and the ratio of BPSA to pPSA to improve cancer detection (U.S. application Ser. No. 09/303,339), the contents of which are incorporated herein in their entirety by reference.

While we had initially conceived that BPSA and pPSA would have specific properties to improve cancer detection, it was unanticipated that inPSA, the remaining free PSA in serum, would show independent diagnostic properties. The finding of improved cancer detection with the various algorithms using BPSA, pPSA and inPSA only became evident once we had measured sufficient cancer and benign samples with BPSA and pPSA assays and analyzed the data. Thus, in the final analysis, the individual forms of pPSA, BPSA and inPSA, both individually and in combination with one another, have shown significantly improved detection of prostate cancer over total and free PSA.

These novel findings suggest a complex relationship between pPSA, BPSA and inPSA in serum. The determination of inPSA can be applied throughout the early diagnostic range of 2–10 ng/ml PSA in order to improve cancer detection and reduce unnecessary biopsies. The examples given in the Results are meant to demonstrate the applicability of inPSA and inPSA combinations with pPSA and BPSA, towards prostate cancer detection, and to suggest some relevant examples of such, but these examples are not meant to limit other potential applications with different ranges of PSA, % free PSA or combinations of pPSA, BPSA and inPSA.

REFERENCES

1. Catalona, W. J., Smith, D. S., Ratliff, T. L., Dodds, K. M., Coplen, D. E., Yuan, J. J. et al. Measurement of prostate-specific antigen in serum as a screening test for prostate cancer. *N Engl J Med,* 1991; 324:1156–61.
2. Labrie, F., Dupont, A., Suburu, R., Cusan, L., Tremblay, M., Gomez, J. L., Emond, J. Serum prostate specific antigen as pre-screening test for prostate cancer. *J Urol,* 1992; 147:846–51.
3. Oesterling, J. E. Prostate-specific antigen: a critical assessment of the most useful tumor marker for adenocarcinoma of the prostate. *J Urol,* 1991; 145:907–23.
4. Lilja, H., Christensson, A., Dahlen, U., Matikainen, M. T., Nilsson, O., Pettersson, K., Lovgren, T. Prostate-Specific Antigen in Serum Occurs Predominantly in Complex with $\square_1$-antichymotrypsin. *Clin Chem,* 1991; 37:1618–25.
5. Stenman, U. H., Leinonen, J., Alfthan, H., Rannikko, S., Tuhkanen, K., Alfthan, O. A complex between prostate specific antigen and $\square_1$-antichymotrypsin is the major form of prostate-specific antigen in serum of patients with prostatic cancer: assay of the complex improves clinical sensitivity for cancer. *Cancer Res,* 1991; 51:222–6.
6. Catalona, W. J., Partin, A. W., Slawin, K. M., Brawer, M. K., Flanigan, R. C., Patel, A. et al. Use of the percentage of free prostate-specific antigen to enhance differentiation of prostate cancer from benign prostatic disease: a prospective multicenter clinical trial. *JAMA,* 1998; 279: 1542–7.
7. Woodrum, D. L., Brawer, M. K., Partin, A. W., Catalona, W. J., Southwick, P. C. Interpretation of free prostate specific antigen clinical research studies for the detection of prostate cancer. *J Urol,* 1998; 159:5–12.
8. Peter, J., Unverzagt, C., Hoesel, W. Analysis of free prostate-specific antigen (PSA) after chemical release from the complex with alpha(1)-antichymotrypsin (PSA-ACT). *Clin Chem,* 2000; 46:474–82.
9. Chen, Z., Chen, H., Stamey, T. A. Prostate specific antigen in benign prostatic hyperplasia: purification and characterization. *J Urol,* 1997; 157:2166–70.
10. Zhang, W. M., Leinonen, J., Kalkkinen, N., Dowell, B., Stenman, U. H. Purification and characterization of different molecular forms of prostate-specific antigen in human seminal fluid. *Clin Chem,* 1995; 41:1567–73.
11. Mikolajczyk, S. D., Grauer, L. S., Millar, L. S., Hill, T. M., Kumar, A., Rittenhouse, H. G. et al. A precursor form of PSA (pPSA) is a component of the free PSA in prostate cancer serum. *Urol,* 1997; 50:710–4.
12. Mikolajczyk, S. D., Millar, L. S., Wang, T. J., Rittenhouse, H. G., Marks, L. S., Song, W. et al. A precursor form of prostate-specific antigen is more highly elevated in prostate cancer compared with benign transition zone prostate tissue. *Cancer Res,* 2000; 60:756–9.

13. Mikolajczyk, S. D., Marker, K. M., Millar, L. S., Kumar, A., Saedi, M. S., Payne, J. K. et al. A truncated precursor form of prostate-specific antigen is a more specific serum marker of prostate cancer. *Cancer Res,* 2001; 61:6958–63.
14. Mikolajczyk, S. D., Millar, L. S., Wang, T. J., Rittenhouse, H. G., Wolfert, R. L., Marks, L. S. et al. "BPSA," a specific molecular form of free prostate-specific antigen, is found predominantly in the transition zone of patients with nodular benign prostatic hyperplasia. *Urol,* 2000; 55:41–5.
15. Mikolajczyk, S. D., Millar, L. S., Marker, K. M., Wang, T. J., Rittenhouse, H. G., Marks, L. S., Slawin, K. M. Seminal Plasma Contains "BPSA", a Molecular Form of Prostate Specific Antigen that is Associated with Benign Prostatic Hyperplasia. *Prostate,* 2000; 45:271–6.
16. Mikolajczyk, S. D., Marks, L. S., Partin, A. W., Rittenhouse, H. G. Free prostate-specific antigen in serum is becoming more complex. *Urol,* 2002; 59:797–802.
17. Nurmikko, P., Vaisanen, V., Piironen, T., Lindgren, S., Lilja, H., Pettersson, K. Production and characterization of novel anti-prostate-specific antigen (PSA) monoclonal antibodies that do not detect internally cleaved Lys145–Lys146 inactive PSA [In Process Citation]. *Clin Chem,* 2000; 46:1610–8.
18. Kumar, A., Mikolajczyk, S. D., Goel, A. S., Millar, L. S., Saedi, M. S. Expression of pro form of Prostate-specific antigen by mammalian cells and its conversion to mature, active form by human kallikrein 2. *Cancer Res,* 1997; 57:3111–4.
19. Stamey, T. A., Teplow, D. B., Graves, H. C. B. Identity of PSA purified from seminal fluid by different methods: comparison by amino acid analysis and assigned extinction coefficients. *Prostate,* 1995; 27:198–203.
20. Bridon, D, Dowell, B. Structural comparison of prostate-specific antigen and human glandular kallikrein using molecular modeling. *Urol,* 1995; 45:801–6.
21. Knott, C. L., Kuus-Reichel, K., Liu, R. S., and Wolfert, R. L. Development of antibodies for diagnostic assays. In: *Principles and Practice of Immunoassay*. Price, C. P. and Newman, D. J. 37–64. 1997. New York, N.Y., Stockton Press. Ref Type: Serial (Book, Monograph)
22. Dawson, J. M. 1999. Clinical Trials: Analysis and Presentation, Presented at the 26th Annual Meeting of the Association of Medical Diagnostics Manufacturers, Available at website of the Association of Medical Diagnostics Manufacturers.
23. Linnet, K. 1999. Necessary sample size for method comparison studies based on regression analysis. *Clin. Chem.,* 45: 882–94.
24. Bland, J. M., Altman, D. G. 1986. Statistical methods for assessing agreement between two methods of clinical measurement. *Lancet,* i: 307–10.
25. Reid, M. C., Lachs, M. S., Feinstein A. R. 1995. Use of methodologic standards in diagnostic test research. Getting better but still not good. *JAMA,* 274: 645–51.
26. Krouwer, J. S. Cumulative distribution analysis graphs—an alternative to ROC curves [Tech Brief]. *Clin. Chem.,* 33: 2305–6.
27. Albert, A. 1982. On the use and computation of likelihood ratios in clinical chemistry. *Clin. Chem.,* 28: 1113–9.
28. Solberg, H. E. 1978. Discriminant analysis. *Crit. Rev. Clin. Lab. Sci.,* 9: 209–42.
29. Matthews, J. N. S., Altman, D. G., Campbell, M. J., Royston, P. 1990. Analysis of serial measurements in medical research. *Br. Med. J.,* 300: 230–5.

We claim:

1. A method to aid in distinguishing prostate cancer from benign prostate disease in a subject, comprising the steps of:
   a) determining the amount of total PSA contained in a serum or plasma sample from the subject;
   b) determining the amount of free PSA in the sample; and calculating the ratio of the free PSA to the total PSA;
   c) determining the amount of inPSA in the sample; and
   d) correlating the amount of inPSA contained in the sample to the presence of prostate cancer in the subject by comparing the amount of inPSA to a predetermined value established with control samples of known cancer and benign disease diagnosis, based on both the level of total PSA and the ratio of the free PSA to the total, wherein inPSA is equal to free PSA minus BPSA and pPSA;
   e) distinguishing prostate cancer from benign prostate disease in the subject based on the correlation in step d).

2. The method of claim 1, wherein step c further comprises the steps of:
   (a) adding sufficient amount of monoclonal antibodies for BPSA and pPSA to the serum or plasma sample to block the BPSA and pPSA contained in the sample; and
   (b) determining the amount of free PSA in the sample, which is the amount of inPSA in the sample.

3. The method of claim 1, wherein step c further comprises the steps of:
   (a) determining the amount of pPSA;
   (b) determining the amount of BPSA; and
   (c) determining the amount of inPSA as the amount of free PSA minus the amount of pPSA and BPSA.

4. The method of claim 3, wherein the correlating step further comprises a step of correlating a mathematical combination of inPSA with total PSA, free PSA, BPSA, or pPSA contained in the sample to the presence of prostate cancer in the subject by comparing the mathematical combination to a predetermined value established with control samples of known cancer and benign disease diagnosis, based on both the level of total PSA and the ratio of the free PSA to the total PSA, wherein the mathematical combination is selected from the group consisting of a ratio of inPSA with pPSA, a ratio of inPSA with total PSA, a ratio of inPSA with free PSA, inPSA minus pPSA, a ratio of inPSA minus pPSA with total PSA, a ratio of inPSA minus pPSA with free PSA, inPSA plus pPSA, a ratio of inPSA plus pPSA with total PSA, a ratio of inPSA plus pPSA with free PSA, inPSA minus BPSA, and inPSA plus BPSA.

5. The method of claim 4, wherein the mathematical combination is a ratio of inPSA with pPSA.

6. The method of claim 3, wherein the pPSA is selected from a group consisting of [−2]pPSA, [−4]pPSA, [−5]pPSA, and [−7]pPSA.

7. The method of claim 4, wherein the mathematical combination is a ratio of inPSA with total PSA.

8. The method of claim 4, wherein the mathematical combination is a ratio of inPSA with free PSA.

9. The method of claim 4, wherein the mathematical combination is inPSA minus pPSA.

10. The method of claim 4, wherein the mathematical combination is a ratio of inPSA minus pPSA with total PSA.

11. The method of claim 4, wherein the mathematical combination is a ratio of inPSA minus pPSA with free PSA.

12. The method of claim 4, wherein the mathematical combination is inPSA plus pPSA.

13. The method of claim 4, wherein the mathematical combination is a ratio of inPSA plus pPSA with total PSA.

14. The method of claim 4, wherein the mathematical combination is a ratio of inPSA plus pPSA with free PSA.

15. The method of claim 4, wherein the mathematical combination is inPSA minus BPSA.

16. The method of claim 4, wherein the mathematical combination is inPSA plus BPSA.

17. The method of claim 4, wherein the mathematical combination is a ratio of inPSA plus or minus BPSA with total PSA or free PSA.

18. The method of claim 1, wherein the total PSA is between 2.5 and 10 ng/ml, the ratio of free PSA to total PSA is greater than 20%, and the amount of the inPSA that is above the pre-determined value is an indication of the presence of prostate cancer.

19. The method of claim 18, wherein the total PSA is between 4 to 10 ng/ml.

20. The method of claim 18, wherein the ratio of free PSA to total PSA is greater than 25%.

21. The method of claim 1, wherein the total PSA is between 2.5 and 10 ng/ml, the ratio of free PSA to total PSA is selected from percentages between 5% and 25%, and the amount of the inPSA that is above or below the pre-determined value is an indicatian of the presence of prostate cancer.

22. The method of claim 21, wherein the total PSA is between 4 to 10 ng/ml.

23. The method of claim 21, wherein the total serum PSA is between 2.5 and 4 ng/ml.

24. The method of claim 21, wherein the ratio of free PSA to total PSA is selected from percentages between 5% and 25%.

25. The method of claim 1, wherein the total PSA is from 1.0 to 10.0 ng/ml.

26. The method of claim 1, wherein the total PSA is below about 20 ng/ml.

27. The method of claim 1, wherein the total PSA is below 10 ng/ml.

28. The method of claim 1, wherein the total PSA is in the range of about 2.5 to 10 ng/ml.

29. The method of claim 1, wherein the ratio of free PSA to total PSA is in the range of 1 to 50%.

30. The method of claim 1, wherein the ratio of free PSA to total PSA is in the range of greater than 20%.

31. The method of claim 1, wherein the ratio of free PSA to total PSA is in the range of greater than 25%.

32. The method of claim 1, wherein the subject is a human.

33. The method of claim 2, wherein the pPSA is selected from [−2]pPSA, [−4]pPSA, or [−5,−7]pPSA.

* * * * *